(12) United States Patent
Liebeck et al.

(10) Patent No.: US 7,479,618 B2
(45) Date of Patent: Jan. 20, 2009

(54) DEVICE FOR HEAT TREATMENT

(75) Inventors: Martin Liebeck, Petersberg (DE); Stefan Uhl, Pfungstadt (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/361,660

(22) Filed: Feb. 23, 2006

(65) Prior Publication Data

US 2007/0023707 A1 Feb. 1, 2007

(30) Foreign Application Priority Data

Feb. 28, 2005 (DE) ................. 10 2005 009 679
Mar. 4, 2005 (DE) ................. 10 2005 010 485

(51) Int. Cl.
*H05B 1/00* (2006.01)
*A47K 10/48* (2006.01)

(52) U.S. Cl. ................. 219/217; 219/222; 219/228; 219/405; 219/411; 219/553; 392/380; 392/410; 392/414; 392/407

(58) Field of Classification Search ................. 219/222, 219/217, 228, 405, 411, 553; 392/380, 410, 392/414, 407; 132/212; 34/68, 96
See application file for complete search history.

(56) References Cited

U.S. PATENT DOCUMENTS 4,382,174 A * 5/1983 Barns ................. 392/410

(Continued)

FOREIGN PATENT DOCUMENTS

EP 0072994 A1 3/1983

(Continued)

OTHER PUBLICATIONS

International Search Report for PCT/IB2006/050503, Jul. 26, 2006 (5 pages).

*Primary Examiner*—Shawntina Fuqua
(74) *Attorney, Agent, or Firm*—Marianne Dressman; Tara Rosnell; Idris N. McKelvey (57) ABSTRACT

Device (1) for the heat treatment of scalp hair (2) of a person (3), consisting of one first and one second heat radiator (11, 12), which are formed and arranged facing each other as a left side radiator (4) and as a right side radiator (5) to provide heat (6) to the side scalp hair (7), wherein the left side radiator (4) has one first ring-shaped infrared radiator (21) with one first shell ring reflector (22) and the right side radiator (5) has one second ring-shaped infrared radiator (21.1) with one second shell ring reflector (22.1), wherein at least one third heat radiator (13) is provided for heat treatment of the remaining scalp hair, wherein all heat radiators (11, 12, 13) are arranged in a so-called open design to provide for unlimited handling and observation of the scalp hair (2) and extensive visual freedom for the person (3) during the heat treatment, characterized in that the first shell ring reflector (22) of this type has at least one first infrared radiation screen (31) and the second shell ring reflector (22.1) has at least one second infrared radiation screen (32) arranged as symmetrical mirror images and on the radiation side, and characterized in that radiation intensity (35) in the area of the contour (36) of an average hairline is gently reduced in the direction of the face (37) of the person (3) (FIG. 4).

4 Claims, 8 Drawing Sheets

U.S. PATENT DOCUMENTS

| | | | |
|---|---|---|---|
| 4,541,442 A | * | 9/1985 | Hollmann et al. ............ 132/212 |
| 4,656,142 A | | 4/1987 | Jaouen et al. |
| 4,910,382 A | * | 3/1990 | Kakuya et al. .............. 219/222 |
| 5,063,688 A | | 11/1991 | Moll et al. |
| D477,111 S | | 7/2003 | Zimmermann |
| 6,606,800 B2 | | 8/2003 | Anthes et al. |

FOREIGN PATENT DOCUMENTS

| | | |
|---|---|---|
| EP | 0156984 B1 | 4/1990 |
| EP | 0372443 A2 | 6/1990 |

* cited by examiner

DEVICE FOR HEAT TREATMENT

BACKGROUND OF THE INVENTION

The invention concerns a device for heat treatment of scalp hair of a person according to the generic term of Claim 1.

These types of devices for treating scalp hair using heat are known in the most varied of embodiments in so-called public designs and are used in hair salons, such as those known, for example, from EP0372443A2, EP0156984A1, EP0072994A1, and EP0105785A.

The device according to US-D477,111-S uses five so-called radiator pots. These radiator pots contain quartz tubes to generate infrared radiation; they also contain reflectors made of aluminum. These features, in conjunction with the correct positioning of the radiator pots with respect to each other, ensure the necessary heat distribution for color, permanent wave, and conditioning treatments. In order to provide the customer with the largest possible freedom of movement and a feeling of openness underneath the heat treatment device, the distance of both radiator pots in the side arms is approximately 18 in (460 mm). In addition, there is a pot in the neck area, an upper pot, to the rear, above the back of the customer's head and an upper pot, in front, above the front of the customer's head.

A disadvantage with these devices can be seen in that at least one part of the face of the person being treated is undesirably impacted with heat radiation and/or that, in addition to heating the product, a large portion of the face of the person being treated is also heated.

SUMMARY OF THE INVENTION

The object of the invention is thus to obtain a generically equivalent device that does not have the disadvantage and/or the object of the invention is to obtain a technical heat treatment device for use in salons that heats the scalp hair of a customer as well as the product on the hair as evenly as possible while simultaneously avoiding any heat radiation of the facial area.

In doing so, the following general technical conditions are indicated:

1. A heat treatment device is constructed from one or more radiator elements.
2. A radiator element consists substantially of one or more radiator tubes made of quartz glass and one reflector.
3. The radiator elements that are located to the right and left of the head are, for cost reasons, identical and are attached as reverse mirror images. Therefore, they must be designed as symmetrical mirror images.
4. Potential optimization parameters are the geometry of the radiator elements, their arrangement, and their performance.

These general conditions severely limit the options for optimization of a given radiation distribution. Pure optimization as stated in the parameters mentioned in Item 4 does not provide satisfactory results. This is due to the fact that the radiation behavior of an exemplary radiation element is, in principle, too diffuse to form a given contour in a satisfactory manner. For this reason, additional measures are required that influence radiation distribution in the desired manner.

This task is achieved by the features of the part indicated in Claim 1 in that the radiation intensity in the area of the contour of an average hairline is allowed to be gently reduced in the direction of the face. A harsh transition in this area would limit the freedom of movement of the person to be treated too severely in relation to the technical results. Additional advantageous progressions of the invention as recited in Claim 1 result from the sub-claims.

BRIEF DESCRIPTION OF THE SEVERAL VIEWS OF THE DRAWINGS

The invention is explained in more detail by means of an embodiment example.

The following is shown.

DESCRIPTION OF THE PREFERRED EMBODIMENT

Figure 1:
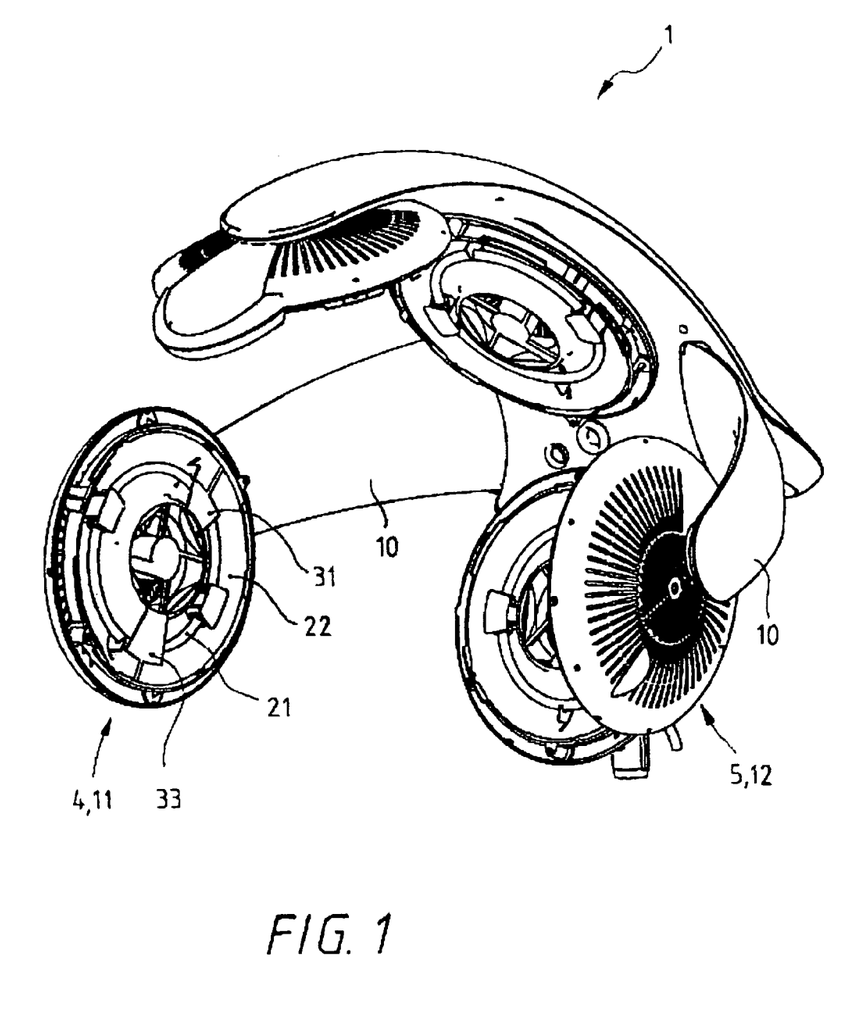
FIG. 1 shows a perspective side view of a device with a view of a side radiator on the left.

FIG. 1 shows a perspective side view of a device 1 with a view of a left side radiator 4 with one first shell ring deflector 22, which has one first ring-shaped infrared radiator 21. The first shell ring reflector 22 has one first and one third infrared radiation screen 31, 33. Each of the two side radiators 4,5 are supported by a support arm 10.

Figure 2:
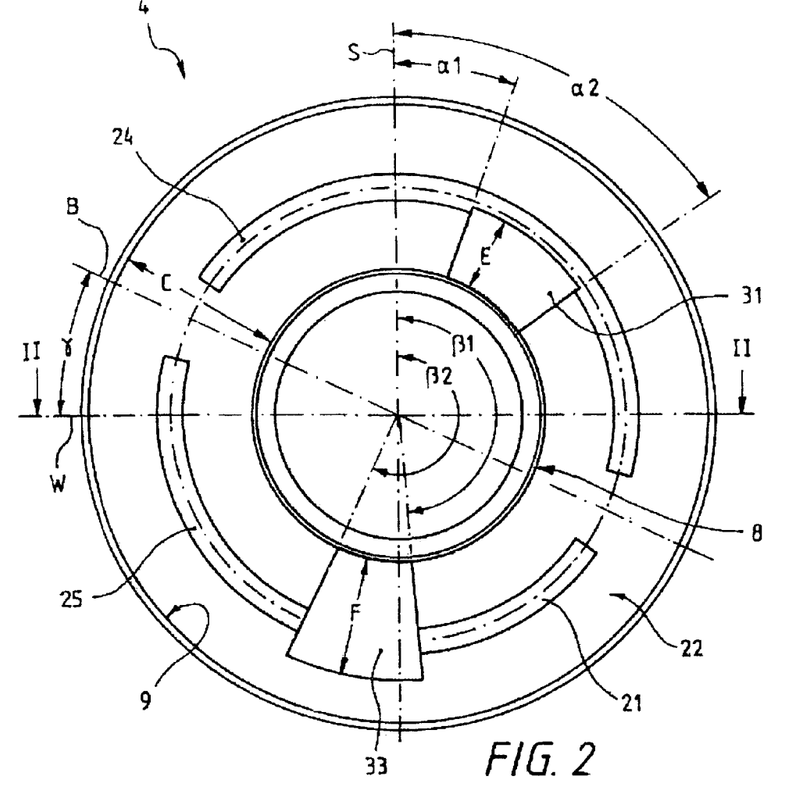
FIG. 2 shows a top view of a left-hand shell ring reflector of the left side radiator with a ring-shaped infrared radiator and one first and third infrared radiation screen.

FIG. 2 contains a top view of a single left-hand shell reflector 22 with one first ring-shaped infrared radiator 21, which contains one first and one third infrared radiation screen 31, 33 on the radiation side.

Figure 3:
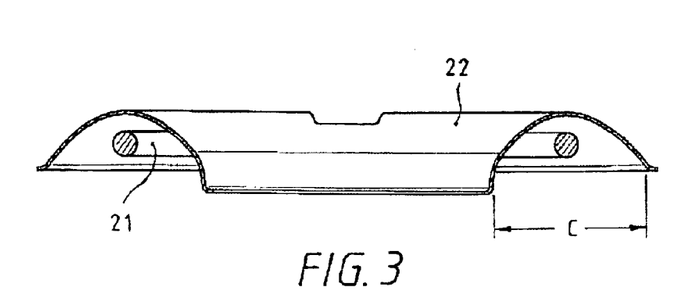
FIG. 3 shows the shell ring reflector in a section II-II according to FIG. 2.

FIG. 3 shows the shell ring reflector 22 in a section II-II according to FIG. 2.

Figure 4:
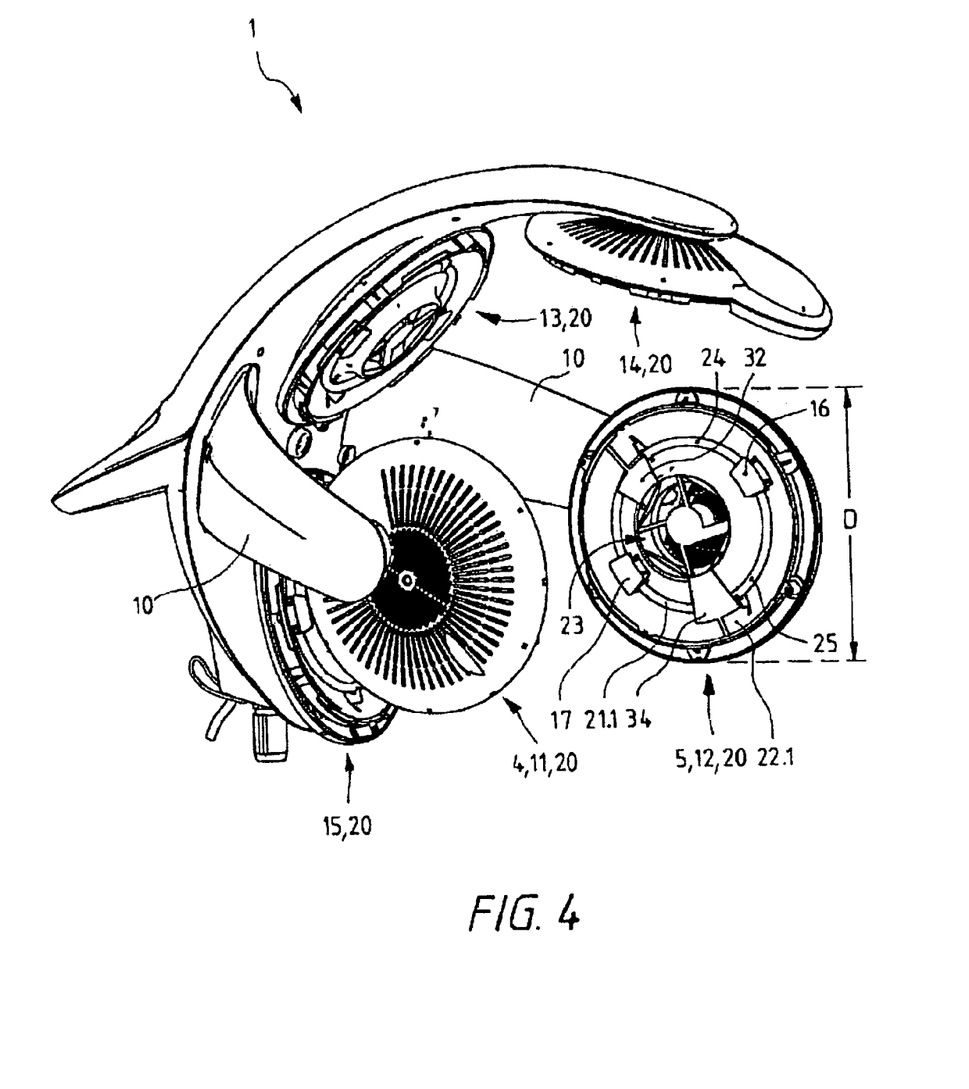
FIG. 4 shows an opposing perspective side view of the device according to FIG. 1 with a view of the right side radiator.

FIG. 4 shows an opposing perspective side view of the device 1 according to FIG. 1 with a view of the right side radiator 5.

Figure 5:
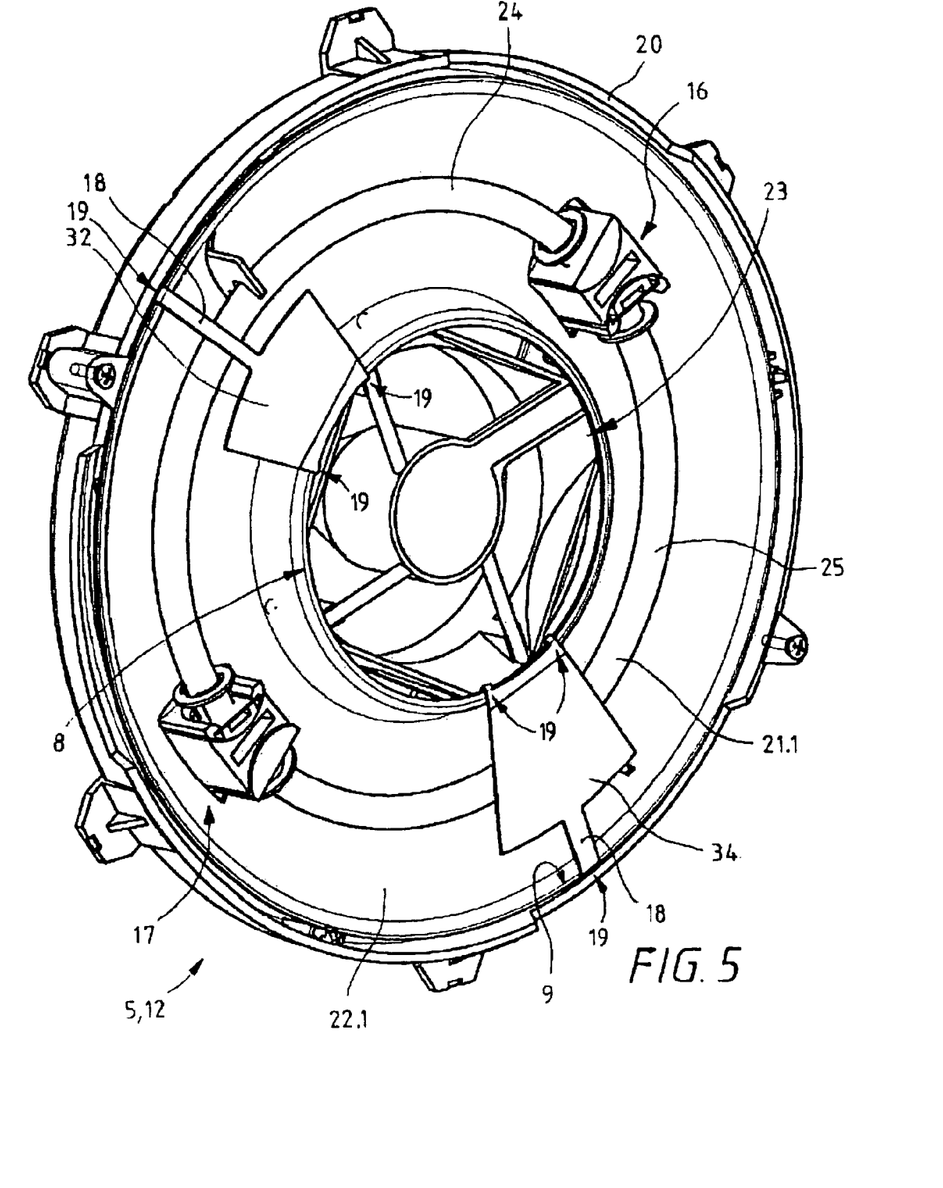
FIG. 5 shows a perspective detailed representation of the right-hand shell ring reflector according to FIG. 4.

FIG. 5 shows a perspective detailed representation of the right-hand shell ring reflector 5 according to FIG. 4. In order to mount the second (or first) and the fourth (or third) infrared screen 32, 34 (31, 33), each of these screens is connected to the interior edge 8 and to the exterior edge 9 of the second (or first) shell ring reflector 22.1 (22) via a bridge 18 using clamps 19.

Figure 6:
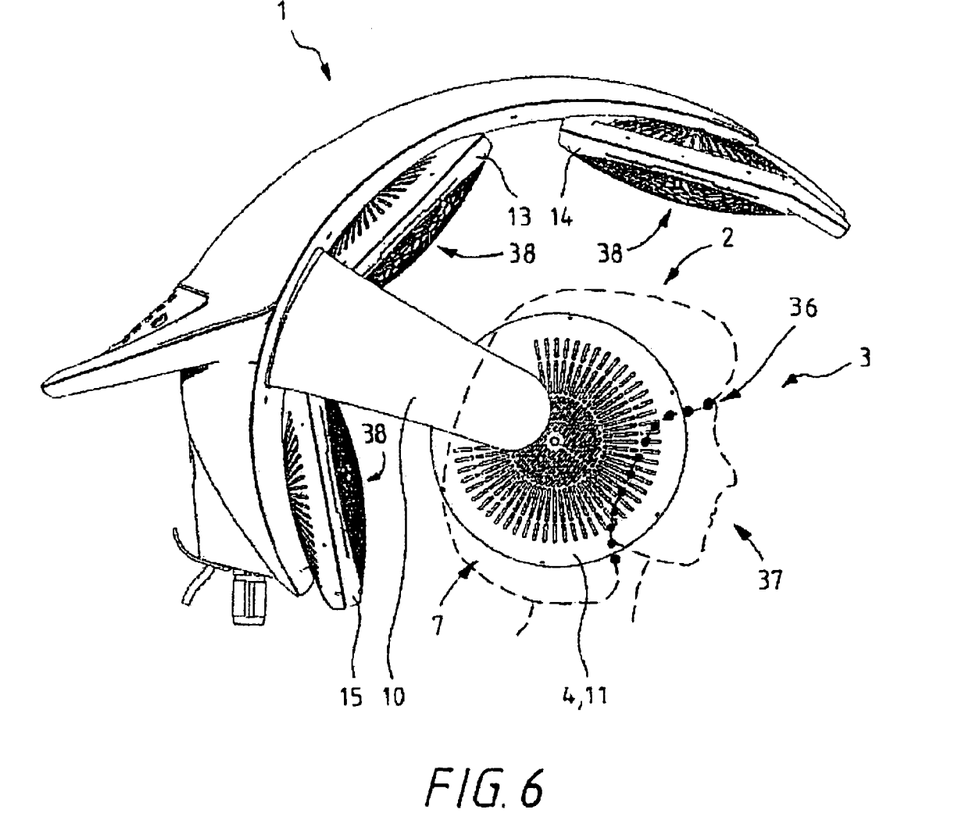
FIG. 6 shows a side view of the device with a person.

FIG. 6 shows a side view of the device 1 with a person 3, wherein the radiation intensity 35 (FIG. 8) in the area of a contour 36 (dotted line) (FIG. 6, 9) of an average hairline decreases gently in the direction of the face 37 of the person 3. Each of the heat radiators 11-15 (FIG. 6, 8) is protected against touch using a cover 38.

Figure 7:
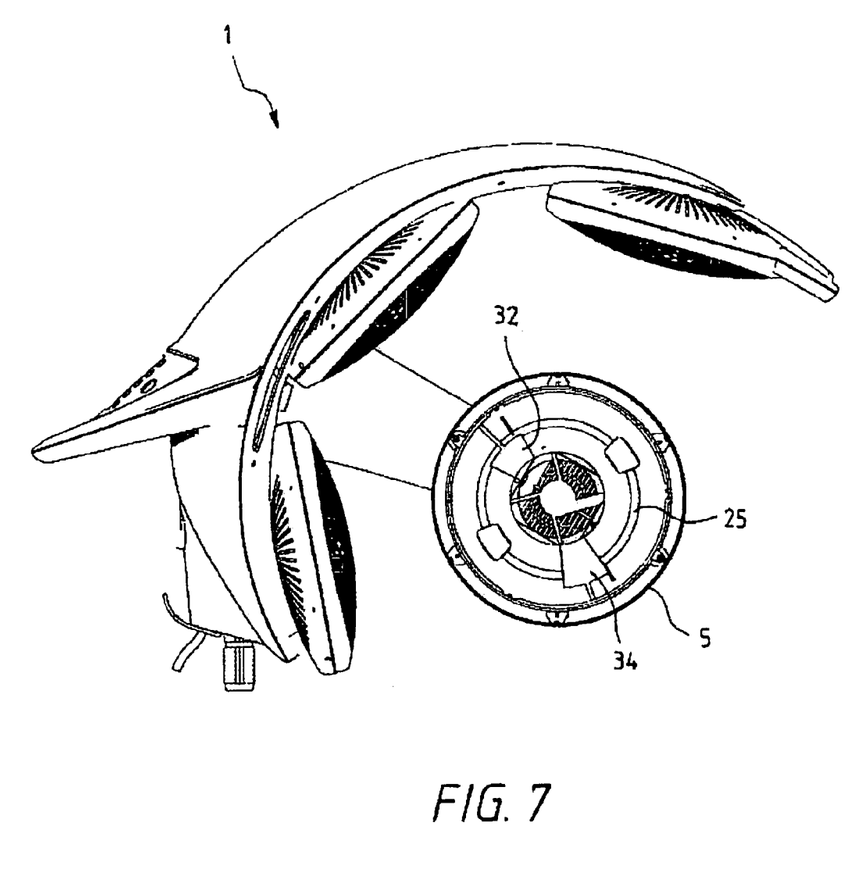
FIG. 7 shows the view according to FIG. 6 but with the left side radiator and arm removed and without the person.

FIG. 7 shows the view according to FIG. 6; however, in order to provide a better view, the left side radiator 4 and arm 10 have been removed and the person 3 is not shown.

Figure 8:
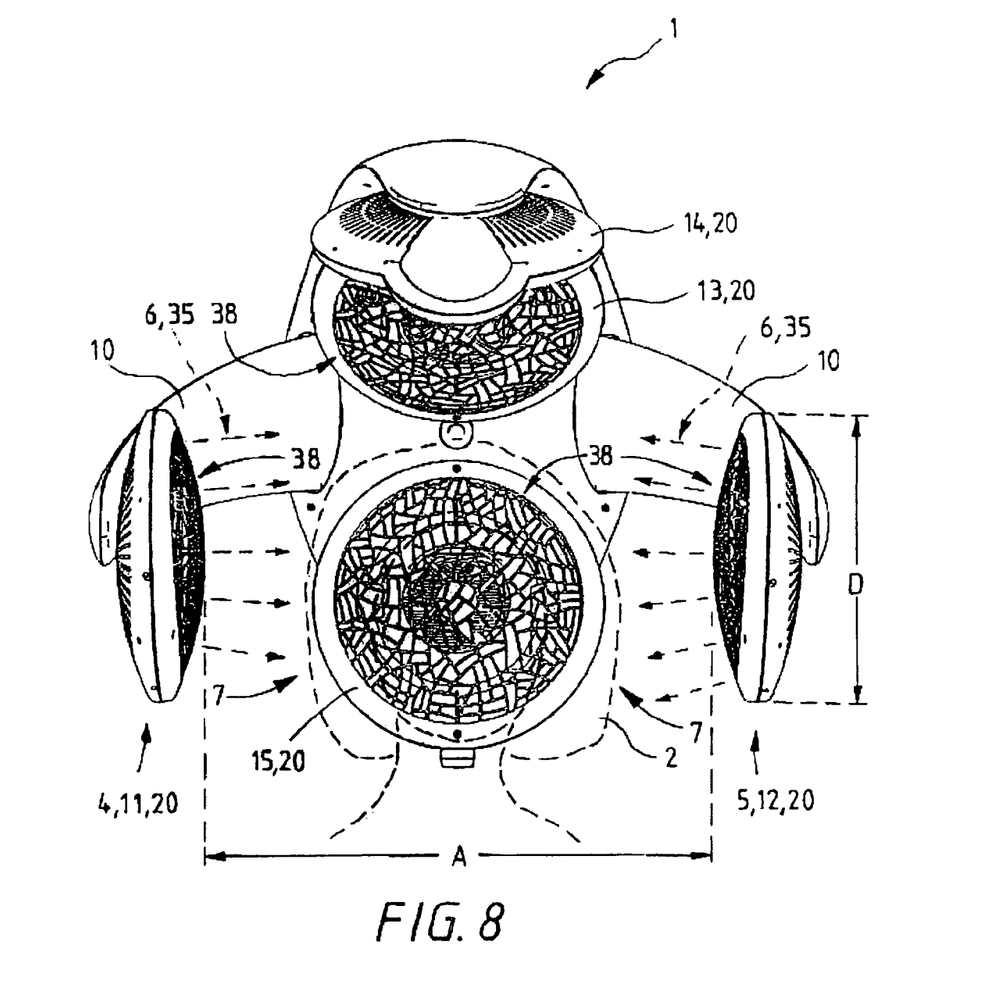
FIG. 8 shows a front view of the device according to FIG. 6.
Figure 9:
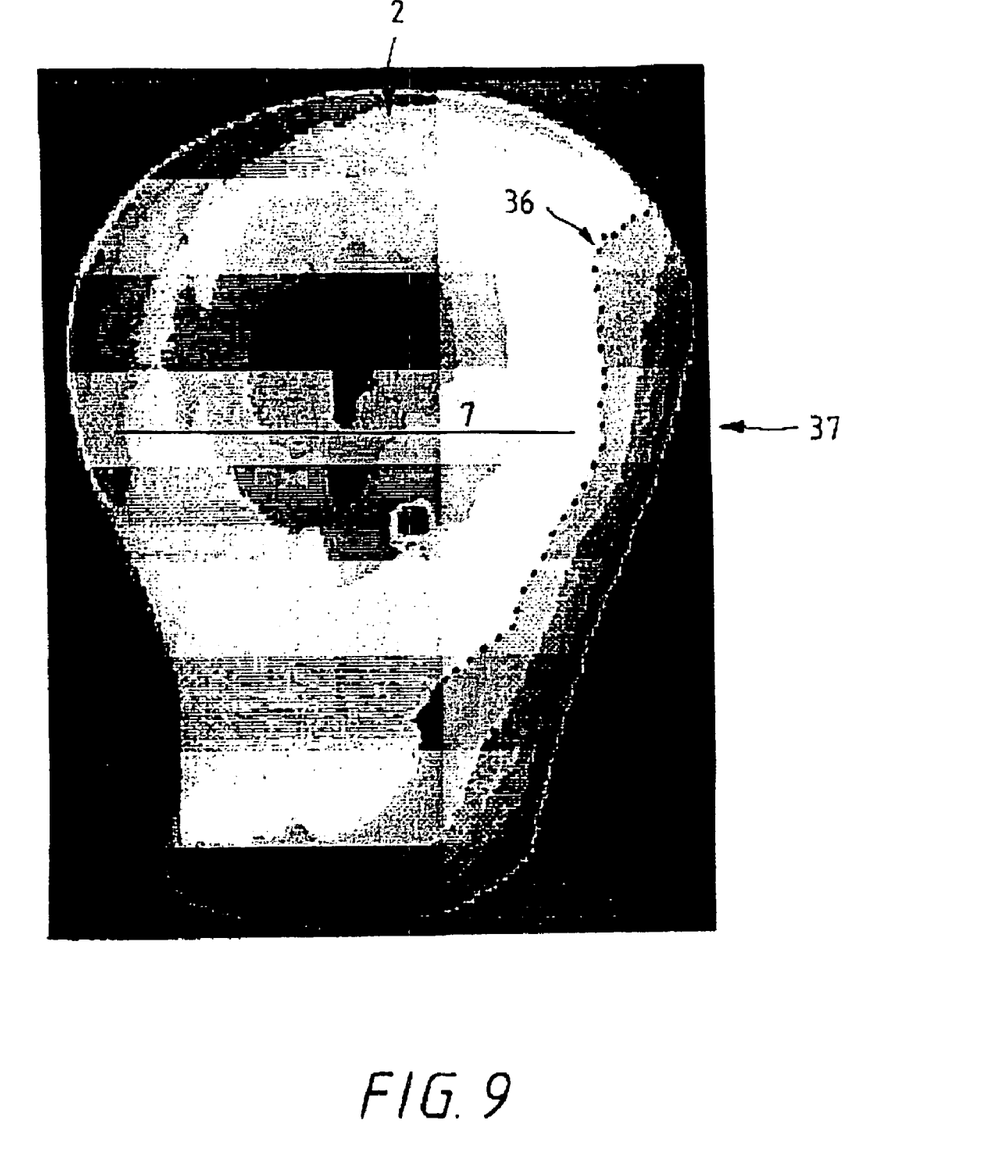
FIG. 9 shows a side view of a head with radiation distribution.

FIG. 8 shows a front view of the device 1 according to FIG. 6.

The figures show a device 1 for the heat treatment of scalp hair 2 of a person 3 (FIG. 6, 8), said device consisting of one first and one second heat radiator 11, 12, which are formed and arranged facing each other as a left side radiator 4 and a right side radiator 5 to provide heat 6 to the side scalp hair 7 (FIG. 8). The left side radiator 4 has one first ring-shaped infrared radiator 21 with one first shell ring reflector 22 and the right side radiator 5 has one second ring-shaped infrared radiator 22.1, wherein at least one third heat radiator 13 is arranged for heat treatment of the remaining scalp hair (FIG. 8). All heat radiators 11, 12, 13 are arranged in a so-called open design in order to provide unlimited handling and observation of the scalp hair 2 and extensive visual freedom for the person 3 during the heat treatment. The first shell ring reflector 22 thus has at least one first infrared radiation screen 31 (FIG. 1) and the second shell ring reflector 22.1 has at least one second infrared radiation screen 32 (FIG. 4), which are arranged as symmetrical mirror images on the radiation side so that radiation intensity 35 (FIG. 8) in the area of a contour 36 (dotted line) (FIG. 6, 9) of the average hairline is gently reduced in the direction of the face 37 of the person 3.

The first infrared radiation screen 31 of the left side radiator 4 has an upper right-side 40 degree angle segment that starts at approximately 20 degrees α1 and continues to approximately 55 degrees α2 (FIG. 2), starting from a vertical S going clockwise, wherein the second infrared radiation screen 32 of the right side radiator 5 is arranged in a symmetrical mirror image (FIG. 4).

The first shell ring reflector 22 (FIG. 2) has a third infrared radiation screen 33 and the second shell ring reflector 22.1 (FIG. 5) has a fourth infrared radiation screen 34 arranged as symmetrical mirror images and on the radiation side.

The third infrared radiation screen 33 of the left side radiator 4 has a left-side 30 degree angle segment that starts at approximately 175 degrees β1 and continues to approximately 205 degrees β2 (FIG. 2), starting with a vertical S in a clockwise direction.

The first or the second infrared radiation screen 31, 32 has a width E that extends from the interior edge 8 of the first or the second shell ring reflector 22, 22.1 up to approximately the first or second ring-shaped infrared radiator 21, 21.1 (FIG. 2).

A third or the fourth infrared radiation screen 33, 34 has a width F that extends from an interior edge 8 of the first or the second shell ring reflector 22, 22.1 up to approximately between the first or second ring-shaped infrared radiator 21, 21.1 and an exterior edge 9 of the first or second shell ring reflector 22, 22.1 (FIG. 2).

Each of the heat radiators 11-15 has the design of a round pot 20, wherein the pot 20 has a diameter D (FIG. 4, 8) of approximately 9.8 in (250 mm).

Each of the heat radiators 11-15 has a fan 23.

Each of the two side radiators 4, 5 has two infrared radiator element half-rings 24, 25, wherein a half-ring axis B of the infrared radiator element half-rings 24, 25 is rotated, in a symmetrical mirror image, around an angle γ of approximately 25 degrees with respect to a horizontal W (FIG. 2).

The infrared radiator element half-rings 24, 25 can be controlled, independently from one another, with electric energy, wherein, in normal operation of the device 1, the top infrared radiator element half-ring (24) is actuated with approximately 70% of 125 Watts and the bottom infrared radiator element half-ring (25) is actuated with approximately 30% of 125 Watts via electric connections 16, 17, whereby the weaker infrared radiation density supports the gentle drop in radiation (FIG. 9) of the area of the hairline in the direction of the face 37 of the person 3 to be treated.

Advantages of the invention:
1. Due to the design measures, the radiation intensity 35 in the facial area 37 of the person being treated 3 is reduced significantly with respect to the areas (scalp hair 2) impacted with the product (FIG. 9).
2. The required radiation distribution of the radiators 11-15 is achieved with the infrared radiators 21, 21.1 by the special geometry of the shell ring reflectors 22, 22.1.
3. The gentle drop in radiation at both side radiators 4, 5 is achieved by at least one screen 31, 32 in front of each of the shell ring reflectors 22, 22.1.
4. The reduction in radiation intensity 35 in the area of the hairline occurs gently in the direction of the face 37 of the person being treated 3 (FIG. 9).
5. Two infrared radiators 21, 21.1, operated with different infrared radiation densities, are installed in each of the side radiators 4, 5, wherein the weaker infrared radiation density supports the gentle drop in radiation of the area of the hairline in the direction of the face 37 of the person being treated 3.

LIST OF REFERENCE CHARACTERS

1 Device
2 Scalp hair
3 Person
4 Left side radiator
5 Right side radiator
6 Heat radiation
7 Side scalp hair
8 Interior edge
9 Exterior edge
10 Arm
11 First heat radiator
12 Second heat radiator
13 Third heat radiator
14 Fourth heat radiator
15 Fifth heat radiator
16 Electric connection
17 Electric connection
18 Bridge
19 Clamp
20 Pot
21 First ring-shaped infrared radiator
21.1 Second ring-shaped infrared radiator
22 First shell ring reflector
22.1 Second shell ring reflector
23 Fan
24 First infrared radiator element half-ring
25 Second infrared radiator element half-ring
31 First infrared radiation screen
32 Second infrared radiation screen
33 Third infrared radiation screen
34 Fourth infrared radiation screen
35 Radiation intensity
36 Contour
37 Face
38 Cover
A Distance
B Half-ring axis
C Reflector width
D Diameter/pot 20
E Width/first, second infrared radiation screen 31, 32
F Width/third, fourth infrared radiation screen 33, 34
S Vertical
W Horizontal
α1 Angle α2 Angle
β1 Angle
β2 Angle
γ Angle All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A device comprising:
   (a) A left side radiator supported by a support arm, the left side radiator comprising:
      (1) One first shell ring reflector comprising a radiation side and an interior edge and an exterior edge;
      (2) One first ring-shaped infared radiator comprising a top infared radiator element half-ring and a bottom infared radiator element half-ring located in a symmetrical mirror image around an angle γ of approximately 25 degrees with respect to a horizontal W of the left side radator when viewed from the radiator side of the left side radiator; the half-rings can be controlled, independently from one another wherein the top infrared radiator element half-ring is actuated with approximately 70% of 125 Watts and the bottom infrared radiator element half-ring is actuated with approximately 30% of 125 Watts;
      (3) One first infared radiation screen with a width E; the first infared radiation screen comprising an upper right-side 40 degree angle segment that starts at approximately 20 degrees α1 and continues to approximately 55 degrees α2, starting from a vertical S of the left side radiator and going clockwise when viewed from the radiator side of the left side radiator;
      (4) One third infared radiation screen with a width F; the third infared radiation screen comprising a left-side 30 degree angle segment that starts at approximately 175 degrees β1 and continues to approximately 205 degrees β2, starting with a vertical S of the left side radiator in a clockwise direction when viewed from the radiator side of the left side radiator;
   wherein the one first infared radiation screen and the one third infared radiation screen are connected to the interior edge of the first shell reflector by a clamp and connected to the exterior edge of the first shell ring reflector by a bridge and a clamp;
      (5) a cover located on the radiator side of the left side radiator;
   (b) a right side radiator supported by a support arm, the right side radiator comprising:
      (1) One second shell ring reflector comprising a radiation side and an interior edge and an exterior edge;
      (2) One second ring-shaped infared radiator comprising a top infared radiator element half-ring and a bottom infared radiator element half-ring located in a symmetrical mirror image around an angle γ of approximately 25 degrees with respect to a horizontal W of the right side radator when viewed from the radiator side of the right side radiator; the half-rings can be controlled, independently from one another wherein the top infrared radiator element half-ring is actuated with approximately 70% of 125 Watts and the bottom infrared radiator element half-ring is actuated with approximately 30% of 125 Watts;
      (3) One second infared radiation screen with a width E; the second infared radiation screen comprising an upper right-side 40 degree angle segment that starts at approximately 20 degrees α1 and continues to approximately 55 degrees α2, starting from a vertical S of the right side radiator and going clockwise when viewed from the radiator side of the right side radiator;
      (4) One fourth infared radiation screen with a width F; the fourth infared radiation screen comprising a left-side 30 degree angle segment that starts at approximately 175 degrees β1 and continues to approximately 205 degrees β2, starting with a vertical S of the right side radiator in a clockwise direction when viewed from the radiator side of the right side radiator;
   wherein the one second infared radiation screen and the one fourth infared radiation screen are connected to the interior edge of the second shell reflector by a clamp and connected to the exterior edge of the second shell ring reflector by a bridge and a clamp;
      (5) a cover on the radiator side of the right side radiator;
   (c) at least one third heat radiator arranged between the left side radiator and the right side radiator such that an open design results.

2. A device according to claim 1, wherein a third or a fourth infrared radiation screen (33, 34) has a width (F) extending from an interior edge (8) of the first or the second shell ring reflector (22, 22.1) up to approximately between the first or second ring-shaped infrared radiator (21, 21.1) and an exterior edge (9) of the first or the second shell ring reflector (22 22.1)

3. A device according to claim 1, wherein each of the heat radiators (11-15) has the design of a round pot (20), which has a diameter (D) of approximately 9.8 in (250 mm).

4. A device according to claim 1, wherein each of the heat radiators (11-15) further comprises a fan (23).

* * * * *